United States Patent [19]

Jenkins et al.

[11] Patent Number: 4,634,556

[45] Date of Patent: Jan. 6, 1987

[54] CRYSTALLINE SODIUM (5R, 6S, 8R)-6-(1-HYDROXYETHYL)-2-(2-CARBAMOYLOXYETHYLTHIO)-PENEM-3-CARBOXYLATE AND PROCESS FOR MAKING SAME

[75] Inventors: John K. Jenkins, Chatham; John S. Chiu, Parsippany; Charles G. Eckhart, Manville; Paul E. McNamara, Westfield; Stanley Rosenhouse, Plainfield; Richard E. Youngstrom, Cedar Grove, all of N.J.

[73] Assignee: Schering Corporation, Kenilworth, N.J.

[21] Appl. No.: 732,533

[22] Filed: May 10, 1985

[51] Int. Cl.$^4$ ................. C07D 499/00; A61K 31/425
[52] U.S. Cl. .................................................... 540/310
[58] Field of Search ................. 260/245.2 R, 245.2 T; 514/192

[56] References Cited

U.S. PATENT DOCUMENTS 4,504,485  3/1985  McCombe et al. .......... 260/245.2 T

*Primary Examiner*—Nicholas S. Rizzo
*Attorney, Agent, or Firm*—Thomas D. Hoffman; Gerald S. Rosen

[57] ABSTRACT

A novel, stable, crystalline sodium (5R,6S,8R)-6-(1-hydroxyethyl)-2-(2-carbamoyloxyethylthio)-penem-3-carboxylate (designated as Form II) is prepared by forming a homogenous solution of sodium (5R,6S,8R)-6-(1-hydroxyethyl)-2-(2-carbamoyloxyethylthio)-penem-3-carboxylate combined with stirring the homogenous solution for a time and at a temperature sufficient to produce Form II and recovering Form II. Form II may also be prepared by contacting a first solution obtained by dissolving (5R,6S,8R)-6-(1-hydroxyethyl)-2-(2-carbamoyloxyethylthio)-penem-3-carboxylic acid in dimethylacetamide with a second solution obtained by dissolving a sodium salt of an organic acid having a pKa of up to about 5, e.g., sodium 2-ethylhexanoate in acetone, in the presence of at least 5 volume percent water while stirring the reaction mixture so formed at a temperature and for a time sufficient to produce Form II followed by recovering Form II.

Form II exhibits a greater physical stability and increased solid state chemical stability and reduced hygroscopicity over that of the amorphous form (e.g., Form I) which renders Form II greatly superior to Form I as a clinically suitable antibacterial agent.

20 Claims, 1 Drawing Figure

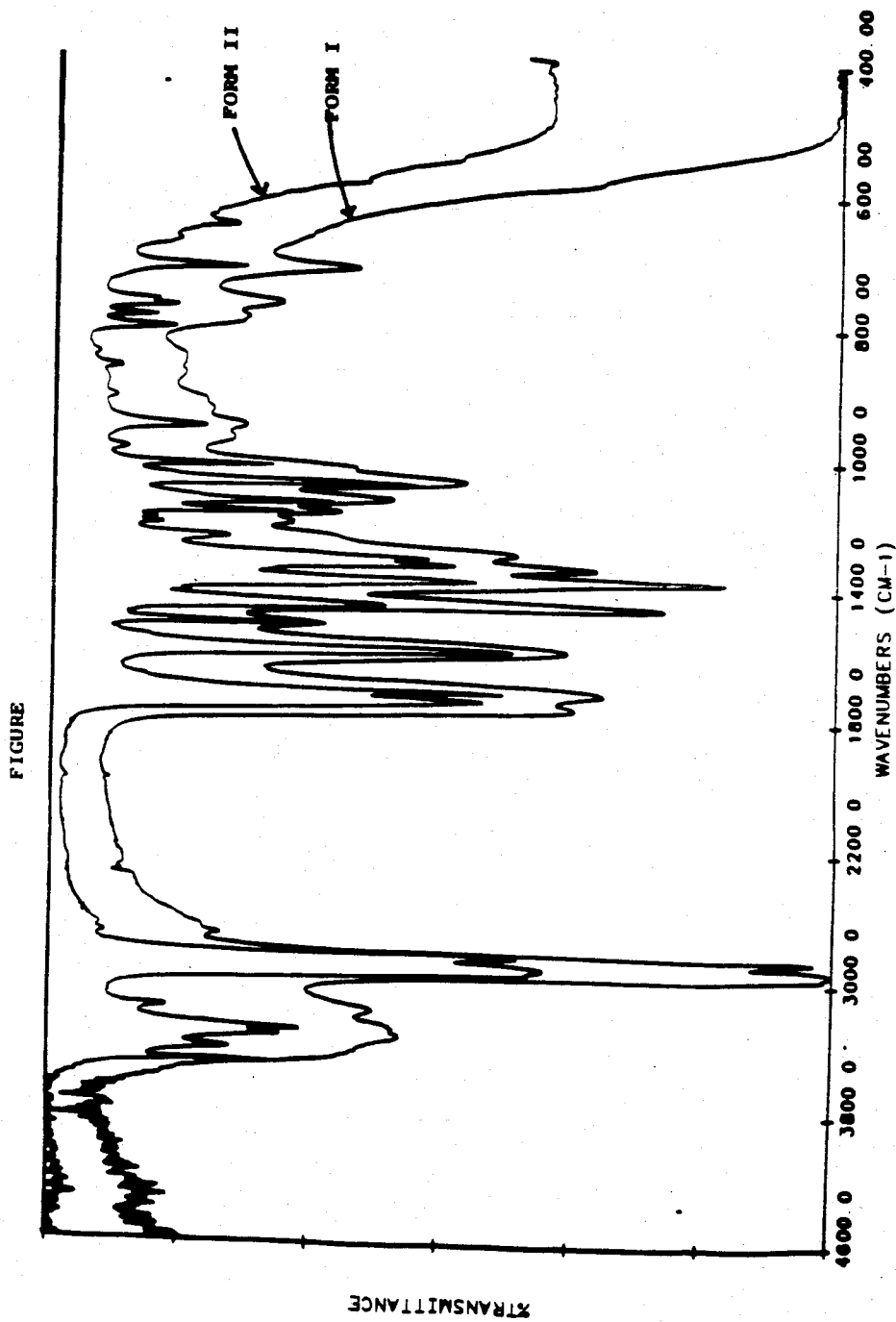

CRYSTALLINE SODIUM (5R, 6S, 8R)-6-(1-HYDROXYETHYL)-2-(2-CARBAMOYLOX-YETHYLTHIO)-PENEM-3-CARBOXYLATE AND PROCESS FOR MAKING SAME

BACKGROUND OF THE INVENTION

The present invention relates to a new, stable, substantially anhydrous crystalline sodium (5R,6S,8R)-6-(1-hydroxyethyl)-2-(2-carbamoyloxyethylthio)-penem-3-carboxylate and processes for its preparation. The crystalline compound exhibits highly desirable physical stability and solid state chemical stability and reduced hygroscopicity which are unexpected and superior to that of amorphous sodium (5R,6S,8R)-6-(1-hydroxyethyl)-2-(2-carbamoyloxyethylthio)-penem-3-carboxylate.

The amorphous compound is useful as a broad spectrum antibacterial effective against beta-lactamase-producing strains. It is prepared by procedures disclosed in U.S. Pat. No. 4,504,485 which patent is hereby incorporated by reference.

The amorphous sodium salt of the subject penem carboxylate has an unsatisfactory shelf-life as compared to extended shelf-life times mandated by the U.S. Food and Drug Administration because it is deliquescent and heat sensitive. These properties make it difficult to prepare and store as clinically suitable formulations.

SUMMARY OF THE INVENTION

The present invention provides a stable substantially anhydrous crystalline sodium (5R,6S,8R)-6-(1-hydroxyethyl)-2-(2-carbamoyloxyethylthio)-penem-3-carboxylate exhibiting an x-ray crystallographic powder diffraction pattern having essentially the following values as shown in Table I:

TABLE I

| Angle of 2θ (degrees) | Spacing d (Å) | Relative/Intensity I/I' |
|---|---|---|
| 7.530 | 11.7392 | 6 |
| 10.833 | 8.1669 | 5 |
| 12.617 | 7.0155 | 50 |
| 13.108 | 6.7538 | 4 |
| 14.625 | 6.0566 | 26 |
| 14.933 | 5.9326 | 4 |
| 16.137 | 5.4924 | 4 |
| 16.825 | 5.2692 | 29 |
| 17.780 | 4.9885 | 11 |
| 18.058 | 4.9122 | 6 |
| 19.544 | 4.5419 | 23 |
| 20.603 | 4.3109 | 36 |
| 21.255 | 4.1802 | 5 |
| 21.600 | 4.1141 | 9 |
| 21.990 | 4.0419 | 8 |
| 23.168 | 3.8390 | 10 |
| 23.926 | 3.7191 | 12 |
| 24.147 | 3.6856 | 100 |
| 24.665 | 3.6094 | 13 |
| 25.031 | 3.5574 | 7 |
| 26.380 | 3.3785 | 23 |
| 27.608 | 3.2309 | 21 |
| 28.181 | 3.1665 | 43 |
| 29.391 | 3.0389 | 13 |
| 30.321 | 2.9477 | 11 |
| 32.434 | 2.7603 | 11 |
| 32.899 | 2.7224 | 9 |
| 33.257 | 2.6939 | 6 |
| 33.909 | 2.6436 | 7 |
| 34.364 | 2.6096 | 6 |
| 34.968 | 2.5659 | 14 |
| 35.411 | 2.5348 | 9 |
| 35.818 | 2.5069 | 13 |

TABLE I-continued

| Angle of 2θ (degrees) | Spacing d (Å) | Relative/Intensity I/I' |
|---|---|---|
| 37.662 | 2.3883 | 16 |
| 39.695 | 2.2705 | 16 |

Since in solution no crystalline form exists, the physicochemical solution characteristics (i.e. nuclear magnetic resonance spectra and specific rotation) of the crystalline and amorphous forms of sodium (5R,6S,8R)-6-(1-hydroxyethyl)-2-(2-carbamoyloxyethylthio)-penem-3-carboxylate are the same and substantially as follows:

(a) $^1$H nuclear magnetic resonance spectrum: $^1$H NMR (D$_2$O) δ: 1.34 (d, 3H), 3.15, 3.30 (d of M, 2H), 3.95 (dd, 1H), 4.31–4.36 (m, 3H) and 5.72 (d, 1H) and (b) a specific rotation as measured at the D line of sodium at 26° C. of about +197° to about +205° at a concentration of about 0.5% in water.

However, the solid state physicochemical characteristics of the crystalline sodium salt of the present invention, Form II, differ from those of the corresponding prior art amorphous sodium salt, Form I, which has decreased thermal stability, no observable x-ray pattern (consistent with an amorphous solid) and a different infrared absorption spectrum, as shown in the FIGURE. The x-ray crystallographic powder diffraction pattern is more definitive than the infrared absorption spectrum for a crystalline material such as the crystalline sodium salt of the present invention (Form II).

The present invention provides a process for preparing a crystalline sodium (5R,6S,8R)-6-(1-hydroxyethyl)-2-(2-carbamoyloxyethylthio)-penem-3-carboxylate which comprises:

(a) forming a homogenous solution of sodium (5R,6S,8R)-6-(1-hydroxyethyl)-2-(2-carbamoyloxyethylthio)-penem-3-carboxylate;

(b) stirring said homogenous solution for a time and at a temperature sufficient to form crystalline sodium (5R,6S,8R)-6-(1-hydroxyethyl)-2-(2-carbamoyloxyethyl thio)-penem-3-carboxylate; and (c) recovering said crystalline sodium (5R,6S,8R)-6-(1-hydroxyethyl)-2-(2-carbamoyloxyethyl thio)-penem-3-carboxylate.

In a preferred aspect of the present invention, there is provided a process for preparing a crystalline sodium (5R,6S,8R)-6-(1-hydroxyethyl)-2-(2-carbamoyloxyethylthio)-penem-3-carboxylate which comprises:

contacting a first solution obtained by dissolving (5R,6S,8R)-6-(1-hydroxyethyl)-2-(2-carbamoyloxyethylthio)-penem-3-carboxylic acid in a first solvent comprising dimethylacetamide with a second solution obtained by dissolving a sodium salt of an organic acid having a pKa in water at 25° C. of up to about 5.0 in a second solvent comprising acetone, in the presence of at least about 5 volume percent water (basis volume of the second solution) while stirring the reaction mixture so formed at a temperature and for a time sufficient to provide crystalline sodium (5R,6S,8R)-6-(1-hydroxyethyl)-2-(2-carbamoyloxyethylthio)-penem-3-carboxylate and recovering the crystalline sodium (5R,6S,8R)-6-(1-hydroxyethyl)-2-(2-carbamoyloxyethylthio)-penem-3-carboxylate.

BRIEF DESCRIPTION OF THE FIGURE

The FIGURE displays the infrared spectra of the crystalline sodium (5R,6S,8R)-6-(1-hydroxyethyl)-2-(2-carbamoyloxyethylthio)-penem-3-carboxylate (Form II) and of the amorphous prior art material (Form I).

DETAILED DESCRIPTION OF THE INVENTION AND OF THE PREFERRED EMBODIMENTS

The composition of matter of the present invention, crystalline sodium (5R,6S,8R)-6-(1-hydroxyethyl)-2-(2-carbamoyloxyethylthio)-penem-3-carboxylate (Form II) can be prepared by forming a homogenous solution of sodium (5R,6S,8R)-6-(1-hydroxyethyl)-2-(2-carbamoyloxyethylthio)-penem-3-carboxylate combined with stirring or agitating the homogenous solution so formed for a time and at a temperature sufficient to form and/or precipitate Form II followed by recovering Form II. The temperatures and times employed are not critical. Normally, room temperature, i.e., about 20°–25° C., is used but temperatures above or below room temperature may also be employed. Generally, to minimize the amount of Form II retained in the mother liquors, the slurry of Form II and mother liquors are cooled to a temperature of about 0°–10° C. to complete the crystallization process. Times of about 2–24 hours are generally sufficient to complete the crystallization but longer times may also be used without deleteriously affecting the process of the present invention. Generally, Form II is collected by filtration followed by washing the filter cake. The solvent residues entrapped in Form II are conveniently removed by vacuum drying at a temperature of about 20°–50° C. In a preferred aspect of the present invention, Form II is dried at 40° C. at high vacuum, i.e., less than about 2 mm Hg, preferably less than about 0.5 mm Hg for about 20–30 hours to remove solvent, i.e., to provide Form II substantially anhydrous, i.e., containing less than about 0.3 to 0.2 weight percent of water and substantially free of organic solvent, i.e., containing no more than about 1 weight percent, preferably less than about 0.6 weight percent of organic solvents. The process of the present invention provides a crystalline form, Form II, that is substantially chemically pure, i.e., less than about 2.0 weight percent, preferably less than about 1.0 weight percent of impurities, has superior bulk handling properties, is resistant to moisture up-take and has increased chemical and physical stability compared to the prior art amorphous form, Form I. Thus, the superior bulk handling properties of the crystalline composition of matter of the present invention readily allows Form II to be milled and ground for preparation of pharmaceutical formulations without atmospheric water up-take. The increased chemical stability of Form II provides retention of potency for long periods and thus, affords increased product shelf-life. The increased physical stability of Form II provides clear solutions without sedimention for trouble-free parenteral injection.

The homogenous solutions of sodium (5R,6S,8R)-6-(1-hydroxyethyl)-2-(2-carbamoyloxyethylthio)-penem-3-carboxylate (hereinafter "sodium penem carboxylate") can be formed by the following Methods:

(A) adding about one volume of an aqueous solution of sodium penem carboxylate to about 15 to about 30 volumes of a $C_3$ or $C_4$ alkanol; or (B) dissolving an amount of sodium penem carboxylate in a sufficient volume of at least one anhydrous polar organic solvent comprising a member selected from Snyder Class II, III, VI solvents or benzyl alcohol; or (C) contacting a first solution of (5R,6S,8R)-6-(1-hydroxyethyl)-2-(2-carbamoyloxyethylthio)-penem-3-carboxylic acid (hereinafter "penem carboxylic acid") with a second solution comprising a sodium salt of an organic acid having a pKa (in water at 25° C.) of up to about 5.0.

When Method (A) is used, isopropanol is the preferred $C_3$ or $C_4$ alkanol. Normally, the concentration of sodium penem carboxylate in water is less than 0.3 weight percent to avoid formation of a non-dispersable gum prior to the formation of crystals of Form II. The volume ratio of water to isopropanol is maintained in the range of about 1:15 to about 1:30. At high water to isopropanol ratios, e.g., about 1:25 to 1:30, precipitation is rapid, but the initial product is amorphous sodium penem carboxylate which slowly converts into the crystalline form (Form II) in about two hours. At lower water to isopropanol ratios, e.g., about 1:15 to 1:20, precipitation of the crystalline form (Form II) is rapid without formation of an amorphous solid. At water to isopropanol ratios of less than about 1:15, no precipitate forms.

The anhydrous polar organic solvents useful in Method (B) are at least one of those selected from Snyder Class II, III, VI solvents or benzyl alcohol as described by L. R. Snyder in *J. Chrom. Science,* Vol. 16, 223–234 (1978) which is hereby incorporated by reference. Particularly useful solvents include methanol (Class II), tetrahydrofuran, (THF) (Class III), benzyl alcohol (Class IV), mixtures of solvents from Classes II and III such as methanol and THF or from Classes I and II such as methyl t-butyl ether and methanol or mixtures of two solvents from the same class such as 2-methoxyethanol and THF. To select the proper volumes of two or more solvents, an amount of sodium penem carboxylate is dissolved in the minimum volume of the first solvent, e.g., from Class II such as methanol and a volume of a second solvent such as methyl t-butyl ether from Class I is added until the cloud point is reached. The solution is heated or additional methanol is added until a clear solution is formed. The solution is thereafter cooled with or without seeding with authentic crystals of Form II until crystals of Form II are observed.

For Methods (A) and (B), amorphous or crystalline sodium penem carboxylate (or mixtures thereof) may be used. In a preferred aspect of Method (B) using a polar solvent such as methanol, use of amorphous sodium penem carboxylate is preferred. If the purification of crystalline material (which may also contain amorphous sodium penem carboxylate) is desired, higher temperatures may be needed to effect dissolution.

Typical suitable solvents for the first solution of Method (C) include dimethylacetamide (DMA), DMA plus at least one $C_1$ to $C_4$ alkanol, particularly DMA/methanol or DMA/ethanol, DMA plus acetone, DMA plus water or DMA plus water and acetone. Typical suitable solvents for the second solution include methanol, methanol plus less than about 50 volume percent of one or more $C_2$–$C_4$ alkanols, acetone, and acetone plus water.

When DMA plus acetone and water is used in Method (C) the amount of water present during the contacting of the first and second solutions should be at least 5 volume percent, preferably 5 to about 15 volume percent, more preferably about 8 to 12 volume percent.

Water in excess of 15 volume percent may be used but is not preferred because of the increased solubility of sodium penem carboxylate in such high water solutions of DMA/acetone.

Typical suitable sodium salts of organic acids having a pKa in water at 25° C. up to about 5 are those listed in Table 5-8 pages P5-17 to P5-41 of Lange's Handbook of Chemistry 12th Edition, McGraw-Hill New York 1972. Particularly useful sodium salts include sodium acetate, sodium lactate, sodium propionate and sodium 2-ethylhexanoate; sodium 2-ethylhexanoate is preferred.

In one aspect of the Method (C) process of the present invention, the first solution is slowly added to the second. In another aspect of the process of Method (C), the order of addition is reversed. In a preferred aspect, the first solution of the penem carboxylic acid in a first solvent comprising DMA and acetone plus water is added to the second solution of sodium 2-ethylhexanoate in a second solvent comprising water and acetone. In a more preferred aspect, the second solution of sodium 2-ethylhexanoate in acetone plus water (the second solvent) is slowly added to the first solution of the penem carboxylic acid in DMA-aqueous acetone (first solvent). While the concentration of water is about 8 volume percent at the completion of the addition, the water concentration at the initial stages of the addition is higher, e.g., about 10–12 volume percent which favors formation of crystals of Form II.

The x-ray crystallographic powder diffraction pattern of the crystalline form of the present invention is more definitive than its infrared absorption spectrum to identify the crystalline form of the present invention as a unique composition of matter. However, for economic reasons the presence of the crystalline form is more conveniently and quickly confirmed by its unique infrared spectrum compared to that of the amorphous form. As illustrated in the FIGURE, the infrared spectrum of Form II is sharper, i.e., shows reduced line broadening and improved intensity with some changes in the intensity of the maxima as well as additional absorption maxima in the hydroxyl and fingerprint regions.

Interestingly, the sodium penem carboxylate exists in only an amorphous form, Form I, and one crystalline form, Form II. The composition of matter of the present invention may be produced by the processes of the present invention as substantially only the crystalline form (Form II) or mixtures of amorphous (Form I) and crystalline form (Form II). The decomposition temperature of the products produced by the processes of the present invention varies in the range of about 140° C. to about 185° C. Form II provided by preferred Method (C) has a decomposition temperature in the range of about 174° C. to about 185° C.

In moisture up-take and chemical stability (at elevated temperatures) experiments, the crystalline composition of matter of the present invention, Form II, is less hygroscopic and has a greater solid state chemical stability at higher temperatures (e.g., 75° C.) than the amorphous form, Form I, as evidenced by the data in the following Tables II and III.

TABLE II

Hygroscopicity

| Form | Method of Preparation | Time Days | Moisture Uptake (wgt. %) at Various % Relative Humidities (R.H.) | | | | |
|---|---|---|---|---|---|---|---|
| | | | 15% | 35 | 52 | 79 | 95 |
| I | Lyophilized sodium penem carboxylate[1] | 3 | .1 | +3.1 | +8.2 | +23 | +106 |
| | | 7 | −.5 | +2.6 | | | +154 |
| | | 11 | | | +8.4 | +25 | |
| II | sodium 2-ethylhexanoate + penem carboxylic acid from DMA/8% aq acetone[2] (Preparation 9) | 3 | −.1 | +.1 | +.2 | +.2 | +91 |
| | | 7 | — | +.3 | +.2 | +.3 | +120 |
| | | 11 | — | +.3 | +.2 | +.3 | +143 |
| II | sodium 2-ethylhexanoate + penem carboxylic acid frcm DMA/8% aq acetone (Preparation 10)[3] | 3 | 0 | +.2 | 0 | +.1 | +90 |
| | | 7 | 0 | +.2 | 0 | +.2 | +122 |
| | | 11 | 0 | +.2 | 0 | +.2 | +139 |

Footnotes to Table II
[1]Initially contained 5.1 wgt % $H_2O$.
[2]Initially contained 0.2 wgt % $H_2O$ after drying at 39° C. for 14 hours at <0.5 mm Hg.
[3]Initially contained 0.1 wgt % $H_2O$ after drying at 39° C. for 16 hours at <1 mm Hg.

From examination of the data reported in Table II, it is evident that the lyophilized amorphorous sodium penem carboxylate (Form I) exhibits noticeable hygroscopicity even at moderate % R.H. The crystalline sodium penem carboxylate (Form II) of the present invention is non-hygroscopic even at 79% R.H.

TABLE III

Chemical Stability at Elevated Temperatures

| | | | Stability Test Conditions | | |
|---|---|---|---|---|---|
| Experiment | Form | Method of Preparation | Time (days) | Temp. (°C.) | Recovery % of Initial[a] |
| 1 | I[1] | Lyophilized sodium penem carboxylate | 14 | 55 | 88 |
| 2 | I | Lyophilized sodium penem carboxylate | 7 | 75 | 0 |
| 3 | I[2] | Lyophilized sodium penem carboxylate | 14 | 55 | 0 |
| 4 | II | Preparation 4 | 14 | 55 | 87 |
| 5 | II | " | 7 | 75 | 74 |
| 6 | II | Preparation 7 | 7 | 35 | 99 |
| 7 | II | " | 7 | 55 | 93 |
| 8 | II | " | 7 | 75 | 80 |
| 9 | II | Preparation 8 | 7 | 55 | 98 |
| 10 | II | " | 21 | 55 | 95 |
| 11 | II[3] | " | 7 | 75 | 96 |
| 12 | II[4] | Preparation 9 | 7 | 75 | 87 |
| 13 | II | " | 7 | 75 | 98 |
| 14 | II[5] | " | 7 | 75 | 97 |
| 15 | II[6] | " | 7 | 75 | 97 |
| 16 | II[7] | Preparation 10 | 7 | 75 | 98 |

TABLE III-continued

Chemical Stability at Elevated Temperatures

| Experiment | Form | Method of Preparation | Time (days) | Temp. (°C.) | Recovery % of Initial[a] |
|---|---|---|---|---|---|
| 17 | II[8] | " | 7 | 75 | 100 |

Footnotes to Table III
[a] % Retention of Original Potency
[1] Contains 1.2 wgt % $H_2O$
[2] Contains 3.8 wgt % $H_2O$
[3] Use procedure of Preparation 8 to give Form II containing 0.3 wgt % $H_2O$ and 0.5 wgt % iPrOH
[4] Use procedure of Preparation 9 except substitute 5% aq acetone/DMA to give Form II containing 0.4 wgt % $H_2O$, 0.2 wgt % DMA and 0.5 wgt % acetone.
[5] Use procedure of Preparation 9 to give Form II containing 0.2 wgt % $H_2O$, 0.16 wgt % DMA and 0.53 wgt % acetone.
[6] Use procedure of Preparation 9 except substitute 10% aq acetone/DMA to give Form II containing 0.2 wgt % $H_2O$, <0.1 wgt % DMA and 0.4 wgt % acetone.
[7] Use procedure of Preparation 10 to give Form II having a decomposition temperature of 181° C., and containing 0.3 wgt % $H_2O$, 0.18 wgt % DMA and 0.32 wgt % acetone.
[8] Use procedure of Preparation 10 to give Form II having a decomposition temperature of 183° C. and containing 0.2 wgt % $H_2O$, 0.04 wgt % DMA and 0.27 wgt % acetone.

Form I is disclosed in U.S. Pat. No. 4,504,485 as a broad spectrum antibacterial agent of high potency and efficacy. As evidenced by data provided on Tables II and III, Form II exhibits a greater solid state chemical stability and reduced hygroscopicity over that of prior art Form I which renders Form II superior (maintenance of high potency over extended shelf-time) to Form I.

The following examples illustrate the invention and set forth the best mode of practicing the process of the invention.

GENERAL EXPERIMENTAL

Infrared absorption spectra were taken as Nujol Mull (a trade name for mineral oil available from Plough Corporation, Memphis, Tenn.) on a Nicolet FT-Infrared spectrometer Model No. 5DX; the measured frequencies listed below are accurate to ±5 $cm^{-1}$. X-ray crystallographic powder diffraction patterns were taken on a Philips X-ray diffractometer Model No. APD-3520 equipped with radiation source: copper $K\alpha$ 1.5418 Å. Proton nuclear magnetic resonance spectra were taken on a Bruker Model No. AM250. Specific rotations were taken in water on a Rudolph Research Model No. Autopol III. Decomposition temperatures were measured on a Dupont differential scanning calorimeter, Model No. 990.

The amorphous penem carboxylic acid and the corresponding amorphous (lyophilized) sodium salt of the penem carboxylic acid were prepared as described in U.S. Pat. No. 4,504,485. The amorphous (lyophilized) sodium salt of the penem carboxylic acid exhibits an infrared absorption spectrum having bands substantially at the following frequencies: broad absorption maxima in the hydroxyl region at 3433(sh), 3344, 3291(sh) and 3188(s)$cm^{-1}$, broad absorption maxima in the carbonyl absorption region at 1764(s), 1720(s), 1593(s) and 1519(w)$cm^{-1}$ and the following absorption maxima in the fingerprint region: 1461(s)*, 1377(s)*, 1340(s), 1298(s), 1250(sh), 1206(w), 1174(m), 1134(m, br), 1079(s), 1042(sh), 979(w), 930(w), 960(w), 884(w), 861(w), 799(m), 776(m, br) and 725(m)*$cm^{-1}$ (mineral oil mull); notation: s=strong; m=medium; w=weak; br=broad; sh=shoulder; *absorption maxima is due to mineral oil.

The sodium 2-ethylhexanoate was prepared by reaction of 2-ethylhexanoic acid and slightly less than the stoichiometric amount of sodium hydroxide in methanol. The water and methanol were removed by vacuum distillation followed by azeotropic vacuum distillation using ethyl acetate. After high vacuum pumping a hygroscopic foam of sodium 2-ethylhexanoate was obtained.

The assay of the crystalline sodium penem carboxylate recovered was measured by high performance liquid chromatograph (HPLC) versus a pure reference standard.

Moisture content of the crystalline sodium penem carboxylate product was determined by titration with Karl Fisher reagent. Non-aqueous solvent content was determined by gas liquid chromatography (glc).

NON AQUEOUS PROCESSES

Preparation 1

Place 104 mg of lyophilized amorphous sodium penem carboxylate (Form I) and 1 mL of anhydrous methanol in a 5 mL pear-shaped flask equipped for magnetic stirring. Continue stirring until crystallization at room temperature appears complete (1 hr.). Place in refrigerator at +5° C. for 48 hours. Filter, wash and dry product under a stream of nitrogen at RT to give 81 mg of the crystalline form of sodium penem carboxylate (Form II) having and an infrared spectrum substantially the same as that of Form II in the FIGURE.

Preparation 2

Use procedure of Preparation 1 except that dissolve 102 mg of the lyophilized amorphous sodium penem carboxylate in 1.5 mL of methanol. Stir vigorously and add 0.7 ml of methyl t-butyl ether [passed through alumina, (E. Merck, activity Grade I, neutral) immediately prior to use] dropwise until the cloud point is reached. Add 2 drops of methanol to form a clear solution. Continue stirring until crystallization starts. Allow the mixture so formed to stand at room temperature for 30 minutes and thereafter place the flask in a refrigerator at +5° C. for 48 hours. Filter, wash [1:1 (v/v) methanol:-methyl t-butyl ether] and dry to give 78.6 mg of crystalline sodium penem carboxylate (Form II) having and substantially the same infrared spectrum as that of Form II in the FIGURE.

Preparation 3

Use the procedure of Preparation 1 except that add 1 g of lyophilized amorphous sodium penem carboxylate (Form I) having a decomposition temperature of 130°–132° C. to an amount of the below-listed solvents sufficient to form a clear solution. The dried crystals of Form II have needle shape and have a infrared spectra substantially the same as that of Form II of the FIGURE.

TABLE IV

| Solvent ml (v/v) | Recovery % | Color | Dec. Temp. (°C.) |
|---|---|---|---|
| 5 mL of 1:1 MeOH:THF[a,b] | 82 | Tan | 133–143 |
| 5 mL of MeOH[a] (continued) | 84 | Light tan | 149–153 |
| 2.9 mL of 2:3* | 78 | Off-white | 153–156 |

TABLE IV-continued

| Solvent ml (v/v) | Recovery % | Color | Dec. Temp. (°C.) |
|---|---|---|---|
| MeOEtOH:THF[b,c] | | | |

Footnotes to Table IV
[a]MeOH is methanol
[b]THF is tetrahydrofuran
[c]MeOEtOH is 2-methoxyethanol
*1.5 g of lyophilized amorphous sodium penem carboxylate was used.

Preparation 4

Add 10.00 g (29.29 mmoles) of amorphous form of (5R,6S,8R)-6-(1-hydroxyethyl)-2-(2-carbamoyloxyethylthio)-penem-3-carboxylic acid (decomposition temperature 153.5°–155° C., HPLC purity of 99.6%) and 20 mL of dimethylacetamide (DMA) to a 125 mL Erlenmeyer flask equipped for magnetic stirring. Stir the mixture at room temperature until a homogenous solution is formed and add thereto 30 mL of anhydrous methanol (MeOH).

Add 3.00 g (36.75 mmoles, 1.22 of stoichiometric amount) of anhydrous sodium acetate (anhydrous powder, reagent grade) and 70 mL of anhydrous methanol to a 250 mL Erlenmeyer flask equipped for magnetic stirring. Stir the mixture so formed at room temperature until a homogenous solution is formed and add thereto 60 mL of anhydrous isopropanol (iPrOH). Add the DMA-MeOH solution of the penem carboxylic acid over a 10 minute period to the stirred MeOH-iPrOH solution of sodium acetate (NaOAc). Observe that some turbidity occurs as the penem carboxylic acid is added, but the turbidity quickly disappears as the sodium penem carboxylate forms. Add seeds of crystalline sodium penem carboxylate (Form II) and continue stirring at room temperature for 7 hours until the crystallization process is complete. Vacuum filter the crystalline product using a Buchner funnel. Wash the filter cake with iPrOH to remove acetic acid, excess NaOAc and DMA. Draw down the filter cake to remove excess solvent and vacuum dry [<0.5 mm Hg at room temperature (24° C.)] for 16 hours to give 9.92 g. (93%) of the crystalline sodium penem carboxylate having an infrared spectrum substantially the same as that of Form II in the FIGURE, a decomposition temperature of 162.5°–163.5° C. and containing 0.3 wgt% DMA, 1 wgt% MeOH, 0.3 wgt% iPrOH and <0.1 wgt% H$_2$O.

A maximum of about 7% of the sodium salt remained in the mother liquors; 3.5% of crystalline penem-carboxylic acid is recovered by adsorption onto and elution from a column containing an XAD-7 resin, the tradename of a polymeric resin available from Rohm and Haas.

Sterile filtrations [Millipore Fluoropore membrane, (0.2μ)] of the DMA-MeOH solution of the penem carboxylic acid and of the MeOH-iPrOH solution of NaOAc prior to combination thereof would provide a sterile product.

Preparation 5

Use the procedure of Preparation 4 except that add a solution of 1 g of penem carboxylic acid in 3 mL of DMA to a solution of 0.3 g of NaOAc in 17 mL of MeOH to give the crystalline sodium penem carboxylate (Form II) in 45% yield having an infrared spectrum similar to the sodium penem carboxylate of Preparation 4 and a decomposition temperature of 174°–175° C.

Preparation 6

Use the procedure of Preparation 4 except use 1 g of penem carboxylic acid and substitute 0.6 g of sodium 2-ethylhexanoate for NaOAc and vary the various solvent volumes as shown in Table V.

TABLE V

| Run # | Solvents for Acid[1] | | Solvents for Salt[2] | | Dec. Temp.[3] (°C.) | Yield (%) | IR[4] |
|---|---|---|---|---|---|---|---|
| | DMA (mL) | MeOH (mL) | MeOH (mL) | iPrOH (mL) | | | |
| 1 | 3 | — | — | 25 | 118–121 | 100 | Non-cryst[5] |
| 2 | 3 | — | 17 | — | 174–176 | 63 | Cryst[6,7] |
| 3 | 3 | — | 17 | 10 | 170–172 | 88 | " |
| 4 | 3 | — | 8.5 | 8.5 | gum | — | — |
| 5 | 3 | — | 17 | 5 | 163–164 | 75 | Cryst. |
| 6 | 3 | — | 10 | 5 | 160–161 | 89 | " |
| 7 | 2 | 2 | 9 | 3 | 165–166 | 88 | " |
| 8 | 2 | 2 | 6 | 3 | 163–164 | 89 | " |
| 9 | 2 | 3 | 5 | 5 | gum | — | — |
| 10 | 2 | 3 | 5 | 4 | 160–161 | 92 | Cryst. |
| 11 | 2 | 3 | 9 | 6 | 163–164 | 90 | " |
| 12 | 2 | 3 | 13 | 6 | 162–163 | 85 | " |
| 13 | 2 | 3 | 13 | 8 | 160–161 | 86 | " |

Footnotes to Table V
[1]Use 1 g of penem carboxylic acid, decomposition temperature 153.5-155° C.
[2]Use 0.6 g of sodium 2-ethylhexanoate.
[3]Decomposition temperature.
[4]Take infrared spectrum of sodium penem carboxylate.
[5]Noncrystalline as determined by IR.
[6]Crystalline form as determined by IR.
[7]In another run, use procedure of Run #1 except add a solution of 1 g of penem carboxylic acid in 3 mL of DMA to 0.6 g of sodium 2-ethylhexanoate in 25 mL of anhydrous acetone, to give a gum which does not crystallize.

Preparation 7

A 2 L three neck round bottom flask was equipped with a 500 mL addition funnel, overhead mechanical stirrer and nitrogen purge. Charge to the flask 900 mL of anhydrous ethanol (denatured with toluene) and 60.0 g (0.351 mole) of sodium 2-ethylhexanoate. Stir mixture to form a homogenous solution. Dissolve 100.0 g (0.299 mole) of penem carboxylic acid in 200 mL of DMA in a 500 mL Erlenmeyer flask and then dilute the solution so formed with 200 mL of denatured anhydrous ethanol. Pour solution into an addition funnel. Slowly add solution of penem carboxylic acid to the solution of sodium 2-ethylhexanoate over a 20 minute period. Use about 100 mL of ethanol for washes. Add seed crystals of the crystalline sodium penem carboxylate (Form II) to the amorphous sodium salt (Form I) which precipitates initially. Stir the slurry at room temperature for 20 hours to effect transformation of amorphous form (Form I) into the crystalline form (Form II). Vacuum filter the crystalline product using a Buchner funnel.

Wash the filter cake with sufficient denatured ethanol to remove 2-ethylhexanoic acid, unreacted sodium 2-ethylhexanoate and DMA. Draw down the filter cake to remove excess solvent and dry filter cake at room temperature under vacuum (<0.5 mm Hg) for 48 hours to give 98.3 g (92% yield) of crystalline sodium penem carboxylate as fine needles having a decomposition temperature of 141° C.; an infrared spectrum substantially the same as that for Form II shown in the FIGURE; assay (HPLC) of 96.5%; pH:6.4 (50 mg/mL); $[\alpha]_D^{26} +196°$ (c 0.5%, $H_2O$); and containing by glc 0.28 wgt.% DMA, 0.55 wgt.% ethanol and, 0.52 wgt.% $H_2O$.

AQUEOUS PREPARATION

Preparation 8

Dissolve 3.0 g of lyophilized sodium penem carboxylate in 50 mL of water and add, with stirring, 900 mL of isopropanol (iPrOH) to provide a clear solution with slight amount of turbidity [$H_2O$:iPrOH=1:15 (v/v)]. Observe precipitate formation after 20 minutes of stirring. Continue stirring for 50 minutes and add 900 mL of iPrOH [$H_2O$:iPrOH=1:30 (v/v)]. Continue stirring the diluted solution for an additional 20 minutes, filter the precipitate using a medium glass frit Buchner funnel. Wash the precipitate with iPrOH and dry at 50° C. for 16 hours under vacuum to give 2.40 g of sodium penem carboxylate as a cream colored crystalline solid having a rod and needle crystal habit, a decomposition temperature of 171° C., x-ray powder diffraction pattern and an infrared spectrum substantially the same listed in Table I and shown for Form II in the FIGURE, respectively, assay (HPLC) of 99.8%, and containing 0.20 wgt.% iPrOH and 0.50 wgt.% $H_2O$.

Preparation 9

Equip a 2 L three-necked round bottom flask with a 500 mL addition funnel, an overhead mechanical stirrer and nitrogen purge. Charge flask with 1000 mL of 8% aqueous acetone [acetone containing 8% water (v/v)] and 60.00 g (0.361 moles) of sodium 2-ethylhexanoate. Stir the mixture so formed until a homogenous solution is formed. Dissolve 100 g (0.299 moles) of (5R,6S,8R)-6-(1-hydroxyethyl)-2-(2-carbamoyloxyethylthio)-penem-3-carboxylic acid (penem carboxylic acid) in 200 mL of DMA contained in a 500 mL Erlenmeyer flask. Dilute solution so formed with 200 mL of acetone and transfer the diluted solution to an addition funnel. Add seed crystals of the crystalline sodium penem carboxylate (Form II) obtained from a small scale run. Add the DMA/acetone solution of the penem carboxylic acid dropwise over a two hour period to the stirred 8% aqueous acetone solution of sodium 2-ethylhexanoate. After 150 mL of the DMA/acetone solution of the penem carboxylic acid is added, formation of crystals is observed, which becomes heavier with continued stirring. After addition is completed, stir the reaction mixture at room temperature for two hours.

Filter the crystalline product under reduced pressure using a Buchner funnel and wash the filter cake with sufficient acetone to remove the 2-ethylhexanoic acid, excess sodium 2-ethylhexanoate and DMA. Draw down the filter cake to remove excess solvent. Dry the granular crystals at <0.5 mm Hg at room temperature for two hours and then at 39° C. (<0.5 mm Hg) for 20 hours to give 101.1 g (94% yield) of the sodium penem carboxylate as an off-white granular solid having decomposition temperature of 179° C.; an infrared absorption spectrum having bands substantially at the following frequencies: sharp absorption maxima in the hydroxyl region at 3499(s), 3419(s), 3333(s), 3296(s) and 3176(w)cm$^{-1}$; sharp absorption maxima in the carbonyl region at 1745(s, br), 1721(s), 1596(s) and 1519(m)cm$^{-1}$; and the following absorption maxima in the fingerprint region at 1462(s)*, 1386(s)*, 1335(s), 1315(s), 1250(m, br), 1214(w), 1198(w), 1174(m), 1145(m), 1088(s), 1035(m), 995(m), 961(m), (919(w), 873(w), 815(m), 797(m), 782(m), 775(m, sh) 725(m)*, 683(w) and 661(w)cm$^{-1}$, (mineral oil mull); notation: s=strong; m=medium; w=weak; br=broad; sh=shoulder; *absorption maxima identified as due to mineral oil; the x-ray crystallographic powder diffraction pattern displayed in Table I; $[\alpha]_D^{26} +202°$ (c 0.5%, $H_2O$); pH=7.0 (50 mg/ml); 0.2 wgt.% $H_2O$; 0.31 wgt.% acetone; 0.08 wgt.% DMA; and assay of 98.6%.

Although seeding is exemplified, it is not necessary if addition of DMA/water/acetone solution of the penem carboxylic acid is interrupted and stirring is continued for 0.5 to 1.0 hours to allow time for crystallization to occur.

Preparation 10

Dissolve 1.00 kg (2.99 moles) of the penem carboxylic acid in 1.7 L of DMA, 1.0 L of acetone and 0.6 L of distilled water in a vessel. Pass solution (A) so formed through a line containing a 0.2μ filter into a reaction vessel equipped with an overhead mechanical stirrer and a nitrogen purge. Rinse the vessel, the lines and filter twice with 0.5 L of acetone. Dissolve 0.522 kg (3.14 moles) of sodium 2-ethylhexanoate in 9.0 L of acetone and 0.2 L of distilled water in a second vessel. Slowly pass 4 L of solution (B) so formed through same line containing the 0.2μ filter into the reaction stirred vessel containing solution (A). Slowly add up to an additional 1.2 L of solution (B). If no crystallization occurs, interrupt addition of solution (B) and continue stirring for 0.5 to 0.75 hours to allow crystallization to occur. Once crystallization occurs, slowly add the remainder of solution (B) through the filter into the stirred reaction vessel over a 2 hour period. Maintain a temperature of 23° C. to 28° C. in reaction vessel through out the addition. Rinse the second vessel, the lines and filter with two 0.5 L portions of acetone. After the addition is complete, continue stirring the reaction mixture for about 1 hr while maintaining the temperature at 23° C. to 28° C. Filter the crystalline product under reduced pressure and wash the filter cake with five 1 L portions of acetone. Vacuum (1-2 mm Hg) dry the product at 50° C. for 18-24 hours to give 1.01 g kg (94-% yield) of the crystalline sodium penem carboxylate as an off white granular solid solved having a decomposition temperature of 185° C. to 187° C., an infrared spectrum substantially the same as shown for Form II in the FIGURE; assay of 98.8%; $[\alpha]^{26}_D +203°$ (c 0.5%, $H_2O$); pH=6.7 and containing 0.2 wgt% $H_2O$, 0.24 wgt% acetone and a 0.14 wgt% DMA.

We claim:

1. A stable, substantially anhydrous crystalline sodium (5R,6S,8R)-6-(1-hydroxyethyl)-2-(2-carbamoyloxyethylthio)-penem-3-carboxylate exhibiting an x-ray crystallographic powder diffraction pattern having the essentially following values:

| Angle of 2θ (degrees) | Spacing, d Å | Relative Intensities I/I' |
|---|---|---|
| 7.530 | 11.7392 | 6 |
| 10.833 | 8.1669 | 5 |
| 12.617 | 7.0155 | 50 |
| 13.108 | 6.7538 | 4 |
| 14.625 | 6.0566 | 26 |
| 14.933 | 5.9326 | 4 |
| 16.137 | 5.4924 | 4 |
| 16.825 | 5.2692 | 29 |
| 17.780 | 4.9885 | 11 |
| 18.058 | 4.9122 | 6 |
| 19.544 | 4.5419 | 23 |
| 20.603 | 4.3109 | 36 |
| 21.255 | 4.1802 | 5 |
| 21.600 | 4.1141 | 9 |
| 21.990 | 4.0419 | 8 |
| 23.168 | 3.8390 | 10 |
| 23.926 | 3.7191 | 12 |
| 24.147 | 3.6856 | 100 |
| 24.665 | 3.6094 | 13 |
| 25.031 | 3.5574 | 7 |
| 26.830 | 3.3785 | 23 |
| 27.608 | 3.2309 | 21 |
| 28.181 | 3.1665 | 43 |
| 29.391 | 3.0389 | 13 |
| 30.321 | 2.9477 | 11 |
| 32.434 | 2.7603 | 11 |
| 32.899 | 2.7224 | 9 |
| 33.257 | 2.6939 | 6 |
| 33.909 | 2.6436 | 7 |
| 34.364 | 2.6096 | 6 |
| 34.968 | 2.5659 | 14 |
| 35.411 | 2.5348 | 9 |
| 35.818 | 2.5069 | 13 |
| 37.662 | 2.3883 | 16 |
| 39.695 | 2.2705 | 16 |

2. A process for preparing crystalline sodium (5R,6S,8R)-6-(1-hydroxyethyl)-2-(2-carbamoyloxyethylthio)-penem-3-carboxylate which comprises:
   (a) forming a homogenous solution of sodium (5R,6S,8R)-6-(1-hydroxyethyl)-2-(2-carbamoyloxyethylthio)-penem-3-carboxylate;
   (b) stirring said homogenous solution for a time and at a temperature sufficient to form said crystalline sodium (5R,6S,8R)-6-(1-hydroxyethyl)-2-(2-carbamoyloxyethylthio)-penem-3-carboxylate; and
   (c) recovering said crystalline sodium (5R,6S,8R)-6-(1-hydroxyethyl)-2-(2-carbamoyloxyethylthio)-penem-3-carboxylate.

3. The process of claim 2 wherein in the step (a) the homogenous solution is formed by adding about one volume of an aqueous solution of the sodium penem carboxylate to about 15 to about 30 volumes of a $C_3$ or $C_4$ alkanol.

4. The process of claim 2 wherein in step (a) the homogenous solution is formed by dissolving an amount of the sodium penem carboxylate in a sufficient volume of at least one anhydrous polar solvent comprising a solvent selected from Snyder Class II, III, VI solvents or benzyl alcohol.

5. The process of claim 4 wherein anhydrous methanol is used.

6. The process of claim 4 wherein a mixture of methanol and a Snyder Class I Solvent is used.

7. The process of claim 6 wherein the Snyder Class I Solvent is methyl t-butyl ether.

8. The process of claim 2 wherein the homogenous solution is formed by contacting a solution comprising (5R,6S,8R)-6-(1-hydroxyethyl)-2-(2-carbamoyloxyethylthio)-penem-3-carboxylic acid with a solution comprising a sodium salt of an organic acid having a pKa of up to about 5.0.

9. The process of claim 8 wherein the solution comprising the penem carboxylic acid further comprises dimethylacetamide.

10. The process of claim 8 wherein the solution of the sodium salt further comprises acetone, or at least one $C_1$–$C_4$ alkanol.

11. A process of preparing a crystalline form of sodium (5R,6S,8R)-6-(1-hydroxyethyl)-2-(2-carbamoyloxyethylthio)-penem-3-carboxylate which comprises contacting a first solution obtained by dissolving (5R,6S,8R)-6-(1-hydroxyethyl)-2-(2-carbamoyloxyethylthio)-penem-3-carboxylic acid in a first solvent comprising dimethylacetamide with a second solution obtained by dissolving a sodium salt of an organic acid having a pKa in water at 25° C. of up to about 5.0 in a second solvent comprising acetone, in the presence of at least 5 volume percent water (basis volumes of the second solution) while stirring the reaction mixture so formed at a temperature and for a time sufficient to produce crystalline sodium (5R,6S,8R)-6-(1-hydroxyethyl)-2-(2-carbamoyloxyethylthio)-penem-3-carboxylate and recovering the crystalline sodium (5R,6S,8R)-6-(1-hydroxyethyl)-2-(2-carbamoyloxyethylthio)-penem-3-carboxylate.

12. The process of claim 11 wherein the volume percent water is no more than about 15 percent.

13. The process of claim 11 wherein the first solution is added to the second solution.

14. The process of claim 13 wherein the first solution further comprises acetone.

15. The process of claim 13 wherein the second solution comprises at least 5 volume percent water.

16. The process of claim 11 wherein the second solution is added to the first solution.

17. The process of claim 16 wherein the first solution contains the water.

18. The process of claim 11 wherein the sodium salt of 2-ethylhexanoic acid is used.

19. The process of claim 11 which further comprises drying said crystalline sodium (5R,6S,8R)-6-(1-hydroxyethyl)-2-(2-carbamoyloxyethylthio)-penem-3-carboxylate at a temperature and at high vacuum for a time sufficient to remove solvent.

20. The process of claim 19 wherein a temperature of about 50° C. and a vacuum of less than about 2.0 mm Hg is used to remove solvent.

* * * * *